United States Patent
Jensen

[11] Patent Number: 6,003,518
[45] Date of Patent: Dec. 21, 1999

[54] METHOD OF STRENGTHENING AND REPAIRING FINGERNAILS

[76] Inventor: Stephany L. Jensen, 877 N. 50 E., Kaysville, Utah 84037

[21] Appl. No.: 09/285,161

[22] Filed: Apr. 1, 1999

Related U.S. Application Data

[63] Continuation-in-part of application No. 09/086,933, May 28, 1998, Pat. No. 5,924,427.

[51] Int. Cl.$^6$ ..................................................... A45D 29/00
[52] U.S. Cl. ............................ 132/73; 132/73.5; 132/200
[58] Field of Search ........................... 132/73, 73.5, 200, 132/285, 319; 424/61, 401

[56] References Cited

U.S. PATENT DOCUMENTS

| | | | |
|---|---|---|---|
| 4,445,234 | 5/1984 | Ogunro | 132/73 |
| 4,625,740 | 12/1986 | Roth | 132/73 |
| 4,627,453 | 12/1986 | Isler | 132/73 |
| 4,632,134 | 12/1986 | Reid | 132/73 |
| 4,718,957 | 1/1988 | Sensenbrenner | 132/73 |
| 5,005,595 | 4/1991 | Aylott . | |
| 5,121,760 | 6/1992 | Ward . | |
| 5,146,935 | 9/1992 | Rumore et al. . | |
| 5,450,864 | 9/1995 | LaJoie et al. . | |
| 5,613,507 | 3/1997 | Geer et al. . | |
| 5,632,973 | 5/1997 | Keller . | |
| 5,638,835 | 6/1997 | Franz et al. . | |
| 5,658,415 | 8/1997 | Montemurro et al. . | |

*Primary Examiner*—Gene Mancene
*Assistant Examiner*—Pedro Philogene
*Attorney, Agent, or Firm*—Trask, Britt & Rossa

[57] ABSTRACT

A device and method for strengthening a natural fingernail includes a nail reinforcing device made of a pliable and conformable material having a thickness that is less than the thickness of a natural fingernail. The nail reinforcing device can be preformed and shaped to correspond to the shape of a natural fingernail or can be shaped to correspond to the general shape of the natural fingernail to which it is attached or adhered. A method for strengthening a natural fingernail of the present invention comprises applying an adhesive to at least a portion of the bottom (underneath) surface of the free end of the natural fingernail, to at least a portion of the top surface of the natural fingernail, or to at least a portion of the upper surface of the nail reinforcing device. The body of the nail reinforcing device is then positioned and maintained under the natural fingernail so as to provide contact between the upper surface of the nail reinforcing device and the bottom surface of the natural fingernail. The sides of the nail reinforcing device are then folded so as to place the upper surface of the nail reinforcing device in contact with the top surface of the natural fingernail. The sides of the nail reinforcing device may be shaped to form decorative patterns on the top surface of the natural fingernail. The method and device can also be used for reattaching a broken fingernail by attaching or adhering the nail reinforcing device to the bottom surface of the detached and remaining portions of the broken fingernail. The method and device can also be used to repair a damaged fingernail. Once the nail reinforcing device has been attached or adhered to the natural fingernail, a filler material is applied to a portion of the nail reinforcing device underlying a damaged portion of the fingernail.

20 Claims, 2 Drawing Sheets

METHOD OF STRENGTHENING AND REPAIRING FINGERNAILS

RELATED APPLICATION

This patent application is a continuation-in-part of patent application Ser. No. 09/086,933 filed May 28, 1998 now U.S. Pat. No. 5,924,427.

BACKGROUND OF THE INVENTION

1. Field of the Invention

The present invention relates generally to a method and device for reinforcing a natural fingernail. The present invention is also directed to a method and device for reattaching or repairing broken or damaged fingernails.

2. State of the Art

Consumers value the appearance of smooth, nicely shaped fingernails. Many women, in particular, desire long fingernails having such an appearance that also look natural and blend effectively into the size and shape of the finger. Many individuals, however, simply cannot grow long nails or grow nails which are weak and break easily.

Various artificial nails have been proposed for use in strengthening, extending, and/or repairing fingernails. These artificial nails are commonly used to strengthen natural fingernails so as to reduce the possibility of breakage. Alternatively, the artificial nails are used to cover imperfections or breaks in the natural fingernails. Artificial fingernails known in the art can generally be classified into two categories: preformed nails that are applied onto the natural fingernail; and artificial fingernails formed by applying a liquid solution or an adhesive composition to the natural fingernail.

Generally, preformed (prefabricated) artificial nails are applied to the surfaces of natural fingernails. These preformed fingernails typically are made of acrylic, fiberglass, or plastic. Preformed nails, however, possess a number of shortcomings. Since they are not custom-made for every size and shape of finger, they can look unnatural or blend ineffectively into the fingers and hand, making them aesthetically unappealing. Additionally, because they are typically adhered to the exposed (top) portion of a natural nail, they tend to fall off or become dislodged fairly easily. This makes them particularly ineffective at strengthening or protecting the natural nail and necessitates constant replacement of the artificial nail.

Two major drawbacks of preformed artificial nails involve their method of application. When these products are adhesively applied onto the majority of the upper exposed surface of the natural nail, air pockets typically form between the artificial nail and the natural nail. These air pockets cause the artificial nail to lift off the surface of the natural nail. This can create discomfort and become aesthetically displeasing to the wearer. More significantly, if the artificial nail remains on the natural nail with air pockets captured therebetween, bacteria and fungus can collect in the air pockets, which can result in damage to the natural nail and/or cuticle. Where an artificial nail is adhered on the leading edge portion of the natural nail, it is difficult to get a smooth blend from the surface of the natural nail onto the plastic nail because a ridge is created where the artificial nail meets the natural nail. The formation of this ridge is particularly noticeable once the natural nail grows out and pushes the ridge away from the cuticle and to an area of the nail that is more visible.

The other category of artificial nails consists of forming an artificial nail in situ (directly on the nail) on the natural fingernail. Artificial nails that are formed in situ employ a form, usually made of plastic, around which the composition is applied and allowed to harden. A manicurist or beauty professional then applies a coating of adhesive to the top surface of a natural fingernail and to the top surface of a fingernail extension.

This type of formed artificial nail, however, also has a number of drawbacks. For example, formation of this type of artificial nail is time consuming and requires a skilled professional or a person having experience in such artificial nail formation methods. Because most artificial nails do not usually last longer than about a week, constant repeat visits to a cosmetician are required. Additionally, when an artificially formed nail breaks off or becomes damaged, the wearer must wait until a visit is scheduled with a cosmetician to repair or replace the artificial nail.

While the results obtained from forming an artificial nail are more aesthetically pleasing than those obtained with application of a preformed nail, a less than perfect integration between the hardened composition, the plastic form, and the natural fingernail nonetheless results from such a formation technique. This is due to the fact that the plastic form, which is usually placed on the tip of the natural nail during the formation process, does not absorb the adhesive and is not integrated into the hardened composition to become one piece. As a result, an integrated, whole nail is not created. Furthermore, if the plastic form comes off, the hardened composition remains, leaving what appears to be a half nail or a nail having two different thicknesses.

An even greater limitation results from the fact that the formed artificial nails are not generally hard enough to protect the natural nail from additional damage or from separating and falling off the natural nail. Thus, application of formed artificial nails does not adequately reinforce the natural nail so as to provide sufficient support to permit growth of long, natural nails.

A general problem with the use of artificial nails, both preformed nails and those that are formed in situ, is that they thicken the natural nail significantly, making it obvious that the wearer has not grown his or her nails naturally. Use of artificial nails which are attached or adhered to the top surface of a natural fingernail can damage the top of the fingernail and/or make the fingernail brittle. Additionally, artificial nails are often difficult or impossible to apply when the user has enlarged, curved nails (i.e., onychogryposis) or eggshell nails (i.e., onychomalacia; soft, thin, white nails that curve down at the free edge of the nail).

A method and device for repairing broken or split fingernails, which does not rely on application of an artificial nail to the top surface of the natural fingernail, is taught in U.S. Pat. No. 5,005,595 issued Apr. 9, 1991 to Aylott ("Aylott"). The device of Aylott requires a support portion for positioning the device underneath a natural nail, a lip for butting the support portion up against the edge of the natural fingernail, and a handle portion attached to the support portion to manipulate the latter. Attachment of the device to the natural fingernail is effected by applying adhesive to the support portion, positioning the lip of the support portion under and up against the edge of the natural fingernail to secure the device thereto, and then removing the handle portion.

The method of Aylott, however, also has a number of shortcomings. The device of Aylott is formed to include three separate parts, that is, a handle portion, a support portion, and a forward surface which is separated from the support portion by a lip. This particular configuration requires specialized molds and, presumably, molding steps which make its production both expensive and time consuming. The configuration of the Aylott device also relies on a handle portion to manipulate and hold the device in place for adhesion to the natural fingernail. During use, however, the handle portion only provides pressure to the central portion of the device and does not provide consistent pressure on the sides of the device. As such, continuous pressure between the entirety of the device and natural fingernail surfaces is not achieved, potentially leaving portions of the device unattached and exposed. The method of Aylott is skill and time intensive since it requires multiple steps to perform. After attachment of the device to the fingernail, the handle portion must be separated from the support portion and the support portion must be shaped to a desired configuration prior to applying a filler material or a finish to the top of the natural fingernail. As with other artificial nails, the device of Aylott is not configured for convenient application to eggshell nails or enlarged, curved nails.

Thus, there still exists a need for a method of strengthening, reattaching, and repairing a natural nail which does not require extensive materials and skill to perform and which can be accomplished conveniently and inexpensively at a moment's notice. A further need exists for a method and device that allows individuals that have difficulty in growing long, strong natural nails which does not rely only on the attachment of materials on the top surface of the natural fingernail and which permits the natural fingernail to grow without the assistance of materials or devices that detract from the natural look of the wearer's fingernails.

BRIEF SUMMARY OF THE INVENTION

The present invention relates to a device and method for strengthening a natural fingernail. The nail reinforcing device comprises a pliable, conformable material having a thickness that is less than the thickness of a natural fingernail. The nail reinforcing device can be preformed and shaped to correspond to the shape of a natural fingernail or can be shaped to correspond to the general shape of the natural fingernail to which it is attached or adhered.

The method for strengthening a natural fingernail of the present invention comprises applying an adhesive to at least a portion of the bottom (underneath) surface of the free end of the natural fingernail or to the upper surface of the nail reinforcing device. The nail reinforcing device is positioned under the natural fingernail so as to provide contact between the upper surface of the body of the nail reinforcing device and the bottom surface of the natural fingernail. Adhesive is also applied to at least a portion of the top surface of the natural fingernail or to at least a portion of the upper surface of the sides of the nail reinforcing device. The nail reinforcing device includes sides that are folded so as to provide contact between the upper surface of the sides of the nail reinforcing device and the top surface of the natural nail. The nail reinforcing device is then maintained in a stable position to ensure adherence between the upper surface of the nail reinforcing device and the bottom and top surfaces of the natural fingernail.

The method can additionally include removing the nail reinforcing device after the natural fingernail has grown out or extended in length and reapplying an adhesive to at least a portion of the bottom surface and/or top surface of the natural fingernail or to at least a portion of the upper surface of a second nail reinforcing device and attaching or adhering the second nail reinforcing device to the extended natural fingernail.

In another embodiment of the method of the present invention, a method for reattaching a broken fingernail comprises applying an adhesive to at least a portion of the bottom and/or top surfaces of a detached portion and a remaining portion of the broken fingernail or to at least a portion of the upper surface of the nail reinforcing device. The nail reinforcing device is then positioned so as to provide contact between the upper surface of the nail reinforcing device and the bottom surface of the detached portion of the fingernail. The nail reinforcing device is also positioned so as to provide contact between the upper surface of the nail reinforcing device and the bottom of the remaining portion of the broken fingernail. The sides of the nail reinforcing device are folded over and adhered to the top surfaces of the detached and remaining portions of the broken fingernail, and the nail reinforcing device is held or maintained in a stable position to ensure adherence between the upper surface of the nail reinforcing device and the bottom and top surfaces of the detached and remaining portions of the broken fingernail.

In another embodiment of the method of the present invention, a method for repairing a damaged fingernail comprises applying an adhesive to at least a portion of the bottom and/or top surfaces of the damaged fingernail or to the upper surface of the nail reinforcing device. The nail reinforcing device is then positioned so as to provide contact between the upper surface of the nail reinforcing device and the bottom surface of the damaged fingernail. The nail reinforcing device is then held or maintained in a stable position to ensure adherence between the upper surface of the nail reinforcing device and the bottom surface of the natural fingernail. Once the nail reinforcing device has been attached or adhered to the natural fingernail, a filler material is applied to a portion of the nail reinforcing device underlying a damaged portion of the fingernail to fill the damaged portion of the fingernail. The sides of the nail reinforcing device are folded over and adhered to the top surface of the damaged and filled nail, and the nail reinforcing device is held or maintained in a stable position to ensure adherence between the upper surface of the nail reinforcing device and the bottom and top surfaces of the damaged and filled fingernail.

In yet another embodiment of the nail reinforcing device of the present invention, the sides of the nail reinforcing device are shaped to form a decorative pattern on the top surface of the natural fingernail once the sides of the nail reinforcing device are folded over and adhered to the top surface of the natural fingernail.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

Figure 1:
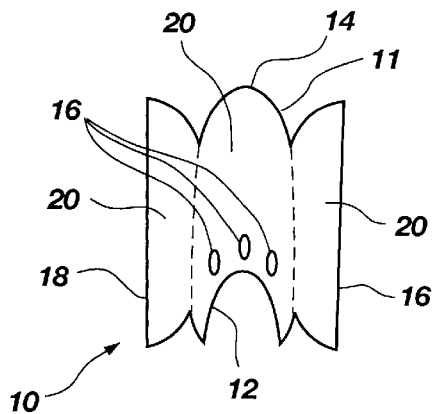
FIG. 1 is a perspective view of a preferred embodiment of the nail reinforcing device of the present invention.

Referring to FIG. 1, a top view of a first embodiment of nail reinforcing device 10 of the present invention is shown. Nail reinforcing device 10 can be formed from a thin sheet of pliable material having sufficient resiliency to conform to the shape of a natural fingernail and having sufficient rigidity to provide support to the natural fingernail after being attached to the latter. Suitable materials for use in making nail reinforcing device 10 include, for example, polymers, acetate, plastic, graphite fiber, vinyl, rubber, or fiberglass. However, nail reinforcing device 10 is most preferably made using silk or linen. Nail reinforcing device 10 has a body 11, a front edge 14, a back edge 12, sides 16 and 18, and an upper surface 20, which includes the upper surface of body 11 and of sides 16 and 18.

Sides 16 and 18 of nail reinforcing device 10 can be of any suitable shape and size. Preferably sides 16 and 18 are shaped so as to provide maximum coverage over and under the corresponding sides of the natural fingernail to which nail reinforcing device 10 is to be attached. Most preferably, sides 16 and 18 are shaped and sized to permit coverage of stress points located at the sides of the natural fingernail lying adjacent to the nail bed, when nail reinforcing device 10 is attached to the natural fingernail.

It is understood that nail reinforcing device 10 may be of any suitable thickness, as desired, which will vary depending on the inherent strength of the material used. Preferably, the thickness of nail reinforcing device 10 is less than the thickness of the natural fingernail and, most preferably, is less than one-half as thick as the natural fingernail. Use of a thin material will enhance the aesthetic appearance of the reinforced fingernail by making nail reinforcing device 10 either imperceptible or barely noticeable. Nail reinforcing device 10 preferably includes holes 15 which facilitate the escape of air trapped between the natural nail and nail reinforcing device 10 upon application of nail reinforcing device 10 to the surface of the natural nail. It is also understood that nail reinforcing device 10 can include gaps, ridges, channels, or any other imprint, texture, or pattern on upper surface 20 that increases the surface area thereof so as to facilitate or enhance adhesion of nail reinforcing device 10 to the natural fingernail.

Nail reinforcing device 10 can be formed and shaped by any suitable means, such as by cutting or sanding, to correspond to the shape of an exposed, lower surface portion (see lower surface 26 of FIG. 2) of the natural fingernail. In this fashion, nail reinforcing device 10 can be preshaped to facilitate its application to the natural fingernail. Alternatively, fingernail reinforcing device 10 can be initially formed in the general shape and size of the natural fingernail being reinforced and then, after adhesion to the fingernail is completed, can be shaped to specifically conform to the contour of the natural fingernail, as more specifically described below with reference to FIGS. 7 and 8. Due to the resilient, pliable nature of nail reinforcing device 10 and the fact that it can be custom-shaped to a desired configuration, nail reinforcing device 10 can be easily applied to a fingernail having any shape and size (e.g., enlarged, curved nails and eggshell nails).

Figure 2:
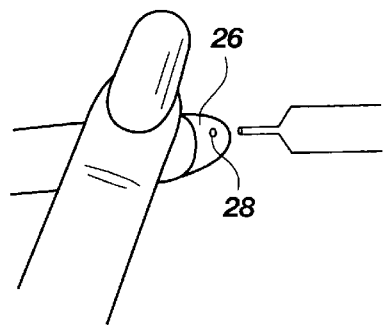
FIG. 2 is a perspective view illustrating application of an adhesive to the bottom surface of the natural fingernail.
Figure 3:
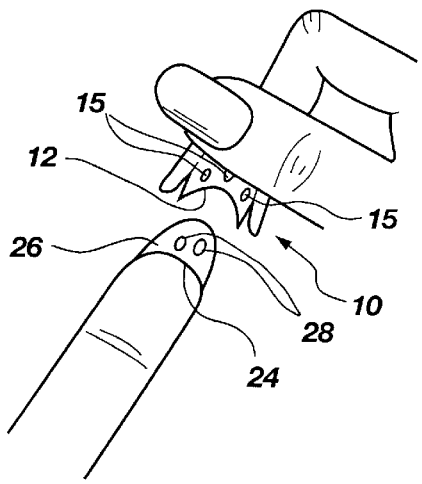
FIG. 3 is a perspective view illustrating the application of the nail reinforcing device to a natural fingernail.
Figure 5:
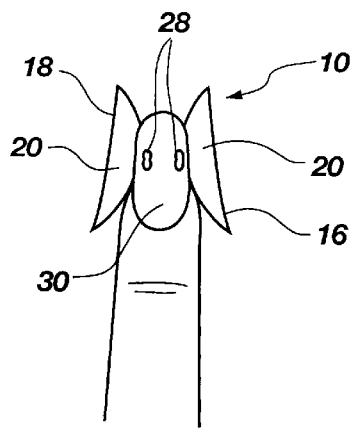
FIG. 5 is a perspective view of the nail reinforcing device attached to the bottom surface of the natural fingernail.

FIGS. 2, 3, and 5 illustrate a method for applying nail reinforcing device 10 to a natural fingernail for purposes of reinforcing the same. As shown in FIG. 2, an adhesive 28, such as an instant glue (e.g., "SUPERGLUE"), is applied to a lower surface (underside) 26 of the natural fingernail. Adhesive 28 can, alternatively, be applied to upper surface 20 at body 11 of nail reinforcing device 10 instead of being applied to lower surface 26. Adhesive 28 can also be applied to both upper surface 20 of nail reinforcing device 10 and lower surface 26. In yet another alternative embodiment, upper surface 20 of nail reinforcing device 10 can be pretreated with adhesive to facilitate application of the same to lower surface 26 of the natural fingernail, thus obviating the need to apply adhesive to either upper surface 20 or lower surface 26 prior to application of nail reinforcing device 10 to the natural fingernail.

As shown in FIG. 3, upper surface 20 of nail reinforcing device 10 is then positioned over lower surface 26 of the natural fingernail, with back edge 12 preferably abutting a portion 24 of the natural fingernail that is in contact with the finger (i.e., hyponychium), so as to maximize contact between nail reinforcing device 10 and lower surface 26. Nail reinforcing device may then be manipulated to smooth any wrinkles in nail reinforcing device, to remove any air trapped between nail reinforcing device 10 and the surface of the natural fingernail or to ensure nail reinforcing device is ideally placed.

Figure 4:
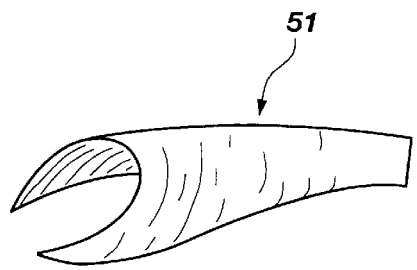
FIG. 4 illustrates a tool useful for manipulating the nail reinforcing device of once the nail reinforcing device is placed in contact with the natural fingernail.

The tool 51, shown in FIG. 4, may be used to manipulate nail reinforcing device 10 after nail reinforcing device 10 is placed in contact with the natural nail. Tool 51 preferably has a smooth surface shaped to generally conform to the underside of the natural fingernail. It is also preferred that tool 11 be thin, sufficiently rigid to exert pressure on nail reinforcing device 10, yet pliable and shapable so that, in the event that tool 11 becomes bonded to nail reinforcing device 10, the cosmetician could leave tool 11 in place and shape substantially rigid tool 11 to conform to the shape and contour of the natural nail.

After being properly positioned over lower surface 26, nail reinforcing device 10 is held in place to ensure good adherence between upper surface 20 of nail reinforcing device 10 and lower surface 26 of the natural fingernail. Holding nail reinforcing device 10 in position can be accomplished by pressing down against reinforcing device 10 with a finger or by utilizing any suitably-configured apparatus or device (e.g., alligator clips, tweezers, etc.) which permits the user to reach under the natural fingernail and press against lower surface 26. Also, any known apparatus (e.g., clamps) can be used to fasten or maintain top surface 20 adjacent to and overlying sides 16 and 18 onto lower surface 26 so as to complete adhesion between nail reinforcing device 10 and the natural fingernail. Alternatively, nail reinforcing device 10 may be held in position by pinching nail reinforcing device 10 between the bottom surface of the natural nail and tool 51 using tweezers, alligator clips, clamps, etc.

As is illustrated in FIG. 5, after nail reinforcing device 10 has been properly placed on the lower surface of the natural fingernail, an adhesive 28, such as an instant glue (e.g., "SUPERGLUE"), is applied to the top surface 30 of the natural fingernail. Adhesive 28 can, alternatively, be applied, to upper surface 20 at sides 16, 18 of nail reinforcing device 10 instead of being applied to the top surface 30 of the natural fingernail. Adhesive 28 can also be applied to both upper surface 20 at sides 16, 18 of nail reinforcing device 10 and to top surface 30 of the natural nail. In yet another alternative embodiment, upper surface 20 of nail reinforcing device 10 can be pretreated with adhesive to facilitate application of the same to the top surface 30 of the natural fingernail, thus obviating the need to apply adhesive to either upper surface 20 or top surface 30.

After adhesive 28 has been placed on upper surface 20 at sides 16 and 18 and/or on top surface 30, sides 16 and 18 are folded over and placed in contact with top surface 30. Folded sides 16, 18 may be manipulated to eliminate any air trapped between the upper surface 20 at sides 16, 18 and top surface 30 of the natural nail and to ensure ideal positioning of folded sides 16,18. Folding over and adhering sides 16,18 to top surface 30 of the natural fingernail is highly desirable because it provides enhanced and substantially evenly distributed reinforcement.

Figure 6:
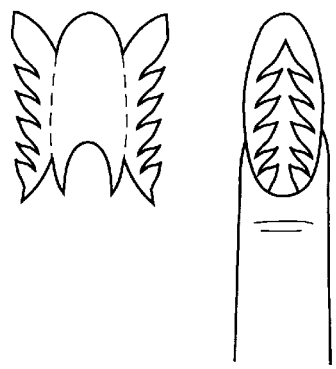
FIG. 6 illustrates a nail reinforcing device sized and shaped to include a decorative pattern once applied to the natural fingernail.

As is illustrated in FIG. 6, sides 16, 18 of nail reinforcing device 10 may be shaped so that a pattern is formed when sides 16, 18 are folded over and adhered to top surface 30 of the natural fingernail. Sides 16, 18 of nail reinforcing device 10 may be preshaped to create various patterns. For example, sides 16, 18 may be pre-shaped to create seasonal patterns (e.g., a Christmas tree, a jack-o-lantern, a heart, a shamrock, etc.), animals, letters, or numbers. Sides 16, 18 of nail reinforcing device 10, may also be custom shaped by a cosmetician to meet individual design needs. It is understood, however, that sides 16, 18 of nail reinforcing device 10 may also include no pattern and may be shaped to serve only reinforcement purposes.

Figure 7:
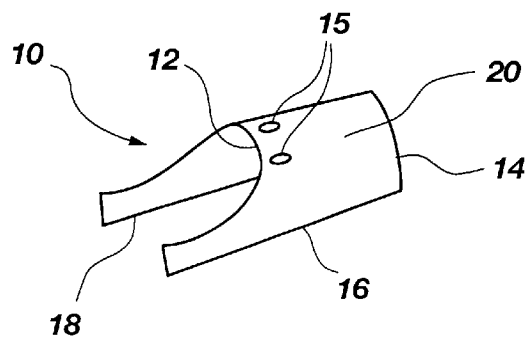
FIG. 7 is a perspective view illustrating another preferred embodiment of the nail reinforcing device attached to the bottom surface of the natural fingernail prior to being shaped to match the contour of the natural fingernail.
Figure 8:
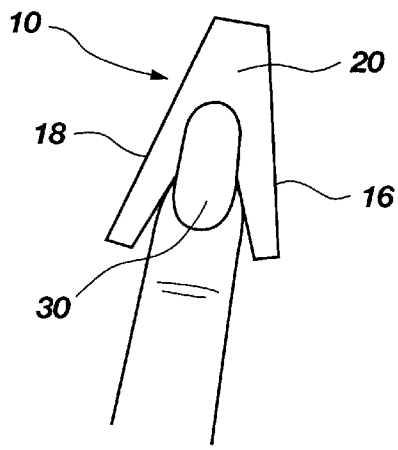
FIG. 8 illustrates the nail reinforcing device of FIG. 7 after being attached to the bottom surface of the natural fingernail.

Nail reinforcing device 10, illustrated in FIGS. 1, 3, and 5, is shown as being preshaped before application. In an alternative method of application, nail reinforcing device 10 is initially formed in a general shape and size that overlaps the natural fingernail being reinforced, as shown in FIG. 7. As shown in FIG. 8, nail reinforcing device 10 is then attached or adhered to lower surface 26 of the natural fingernail following the method previously described in conjunction with FIGS. 2 and 3, and 5. After adhesion to lower surface 26 is completed, sides 16 and 18 of nail reinforcing device 10 can be shaped, such as by cutting with a pair of cosmetic scissors or by filing, to conform to a desired contour and shape. It is also understood that after adhesion of nail reinforcing device 10 to lower surface 26 is completed, sides 16, 18 can be shaped to conform to the contour and shape of the natural fingernail and to create a pattern after being folded and bonded or adhered to top surface 30.

The method of application of nail reinforcing device 10 may also include filing of nail reinforcing device 10 after nail reinforcing device 10 has been applied to a natural fingernail. Where sides 16, 18 are not shaped to form a pattern after being folded, filing of folded sides 16, 18 may be conducted in order smooth or blend nail reinforcing device 10 into the contours of the natural nail. Even where sides 16, 18 form a pattern after folding, filing of folded sides 16, 18 may be conducted, if needed, to smooth or shape nail reinforcing device 10.

Figure 9:
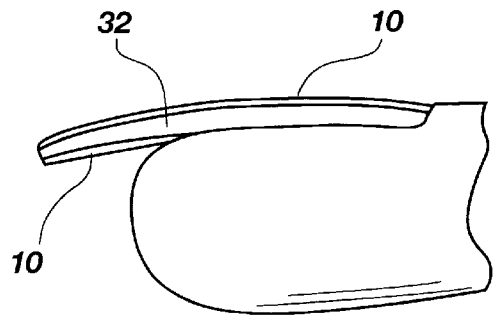
FIG. 9 is a partial diagrammatic section of a natural fingernail which has been reinforced with the nail reinforcing device of the present invention.

As further shown in FIG. 9, which represents a cross-sectional view of a natural fingernail 32 that has been reinforced with nail reinforcing device 10 by the method of this invention, nail reinforcing device 10 has a thickness that is a fraction of the thickness of natural fingernail 32 to which it is attached. In a preferred embodiment, the thickness of nail reinforcing device 10 is from about 2 mils to about 10 mils, which makes nail reinforcing device 10 either hardly visible or not noticeable at all, upon close inspection, in relationship to the natural fingernail to which it is applied.

Figure 10:
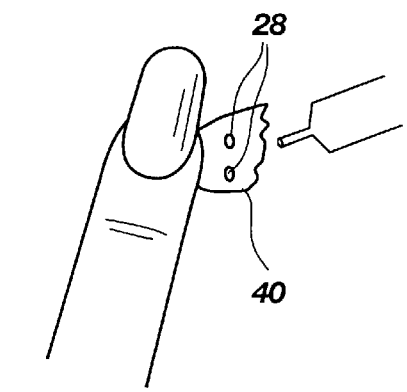
FIG. 10 is a perspective view illustrating application of an adhesive to the bottom surface of the detached portion of a broken fingernail.
Figure 11:
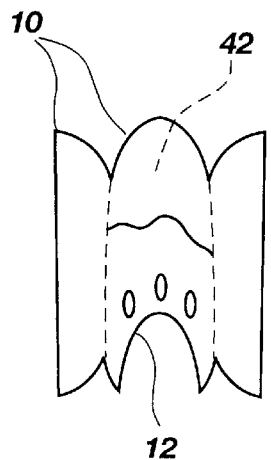
FIG. 11 illustrates a method of reattaching a broken fingernail using the nail reinforcing device.

Referring to FIGS. 10 and 11, the present method of reinforcing a natural fingernail can also be used to reattach a detached portion of broken fingernail. As shown in FIG. 10, this can be accomplished by applying adhesive 26 to detached portion 40 of the broken fingernail. As shown in FIG. 11, nail reinforcing device 10 is then attached onto lower surface (underside) 42 of detached portion 40, so as to position the section of nail reinforcing device 10 containing back edge 12 in an overlapping fashion over detached portion 40 of the broken fingernail. The detached portion 40 and attached nail reinforcing device 10 are positioned over the lower surface of the broken fingernail, with back edge 12 preferably abutting a portion 24 of the natural fingernail that is in contact with the finger, using the same technique described above with reference to FIG. 3. Nail reinforcing device 10 is then held in position in order to ensure good adherence between upper surface 20 of nail reinforcing device 10 and the lower surface of the natural fingernail (see FIG. 3), and sides 16, 18 are folded over and adhered to top surface 30 of the natural fingernail using the same technique described above with reference to FIG. 5.

The present method of reinforcing a natural fingernail can also be used to repair a damaged fingernail (e.g., chipped or cracked fingernail). This can be accomplished by following the techniques described in conjunction with FIGS. 1 through 4. After a preshaped nail reinforcing device 10 has been attached to natural fingernail 32, as shown in FIG. 12, the damaged portion 48 of the natural fingernail can be repaired by applying any suitable strengthening material (e.g., polymeric filler) to the portion of nail reinforcing device 10 underlying damaged portion 48 of the natural fingernail to fill the same.

Alternatively, the method for repairing a damaged fingernail can be accomplished by using a nail reinforcing device 10 that has not been preshaped to conform with the shape of the natural fingernail, attaching nail reinforcing device 10 to the natural fingernail, and repairing the damaged fingernail as described above. After adhesion to natural fingernail 32 is completed, nail reinforcing device 10 can be shaped, such as by cutting with a pair of cosmetic scissors or by filing, to specifically conform to the contour of the natural fingernail to which it is attached.

Figure 12:
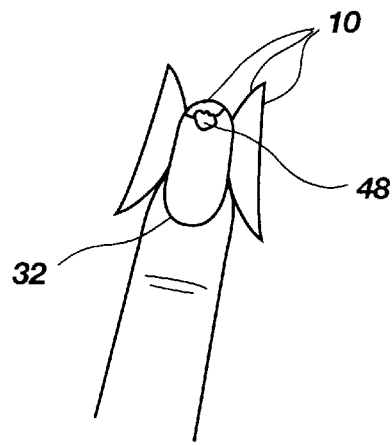
FIG. 12 illustrates a method of repairing a damaged fingernail using the nail reinforcing device.

With reference to the methods described in conjunction with FIGS. 10, 11, and 12, it is understood that adhesive 28 can, alternatively, be applied to upper surface 20 of nail reinforcing device 10 instead of being applied to the lower surface of the natural nail. Adhesive 28 can also be applied to both upper surface 20 of nail reinforcing device 10 and lower surface 26. In yet another alternative embodiment, upper surface 20 of nail reinforcing device 10 can be pretreated with adhesive to facilitate application of the same to lower surface 26 of the natural fingernail, thus obviating the need to apply adhesive to either upper surface 20 or lower surface 26 prior to application of nail reinforcing device 10 to the natural fingernail.

Regardless of its intended use (i.e., strengthening, repairing, or reattachment of a natural fingernail), the application of nail reinforcing device 10 provides the necessary support and structure to a natural fingernail to allow the wearer to grow long fingernails, while at the same time maintaining a natural, aesthetically-pleasing look in the process. Advantageously, use of nail reinforcing device 10 according to the aforementioned methods of application allows natural, unobstructed growth of the natural fingernail and further provides reinforcement of stress points located at the sides of the natural fingernail, particularly where the free edge of the natural fingernail and the nail bed meet. Use of reinforcing device 10 as set forth herein can create an embossed or three-dimensional impression on the top surface 30 of the natural fingernail.

Additionally, as the natural fingernail grows, nail reinforcing device 10 extends with the natural fingernail. Because of this, it is understood that, as nail reinforcing device 10 extends outwardly and away from the finger as the natural fingernail grows, nail reinforcing device 10 can be removed and replaced with a new nail reinforcing device 10 that has been preshaped to conform to the shape of the now larger, exposed, lower surface portion (i.e., lower surface 26 of FIG. 2) of the natural fingernail according to the methods described above. Alternatively, nail reinforcing device 10 can be initially formed to match the overall or general shape and size of the natural fingernail and then, after being attached or adhered to the natural fingernail, shaped to specifically conform to the contour of the natural fingernail.

Nail reinforcing device 10 can be sold in any of the forms mentioned herein (e.g., preshaped, nonshaped, with preapplied adhesive, etc.) either individually or as part of a kit containing a combination of items necessary for the task of reinforcing, reattaching, and/or repairing natural fingernails. A kit can include, for example, one or more nail reinforcing device 10, an adhesive, a pair of scissors or nail file, a device for use in manipulating or pressing nail reinforcing device 10 against the natural fingernail, and a strengthening material.

Although the preferred embodiments of the present invention have been disclosed for illustrative purposes, those skilled in the art will appreciate that various modifications, additions, and substitutions are possible, without departing from the scope and spirit of the invention as disclosed in the accompanying claims.

What is claimed is:

1. A method of strengthening and enhancing a natural fingernail comprising:
   providing a pliable nail reinforcing device having a body, a first side, a second side and an upper surface;
   applying an adhesive to at least a portion of an underneath surface of the natural fingernail, to at least a portion of a top surface of the natural fingernail or to at least a portion of said upper surface of said pliable nail reinforcing device;
   conforming said body of said pliable nail reinforcing device to the curvature of an underneath surface of the natural fingernail so as to provide contact between said upper surface of said pliable nail reinforcing device and the underneath surface of the natural fingernail;
   folding said first side and said second side of said pliable nail reinforcing device so as to provide substantially conforming contact between a top surface of the natural fingernail and said upper surface of said pliable nail reinforcing device; and
   maintaining said pliable nail reinforcing device in a stable position to ensure adherence between said upper surface of said pliable nail reinforcing device, the underneath surface of the natural fingernail, and the top surface of the natural fingernail.

2. The method of claim 1, further comprising shaping said body of said pliable nail reinforcing device to conform to the shape of the underneath surface of the natural fingernail prior to applying an adhesive to the underneath surface of the natural fingernail.

3. The method of claim 1, further comprising shaping said first and second sides of said pliable nail reinforcing device to conform to the contour of the top surface of the natural fingernail after conforming said body of said pliable nail reinforcing device to the curvature of the underneath surface of the natural fingernail.

4. The method of claim 1, wherein said adhesive is applied to said at least a portion of the underneath surface of the natural fingernail, to at least a portion of the top surface of the natural fingernail, and to at least a portion of said upper surface of said pliable nail reinforcing device.

5. The method of claim 1, wherein said first and second sides of said pliable nail reinforcing device are shaped to form a decorative pattern on said top surface of the natural fingernail.

6. A nail reinforcing device for strengthening, enhancing or repairing a natural fingernail comprising:
   a pliable body being curved to substantially match a curvature of an underneath surface of a free edge of the natural fingernail;
   a first edge and second edge on said pliable body, said second edge being shaped to substantially match the arcuate contour of the nail bed; and
   sides on said pliable body, said sides shaped and adapted to bend around sides of the natural fingernail and onto a top surface of the natural fingernail.

7. The device of claim 6, wherein said nail reinforcing device sides are shaped to form a decorative pattern on the top surface of the natural fingernail.

8. The device of claim 7, wherein said pattern comprises a three-dimensional design.

9. The device of claim 7, wherein said pattern comprises an alphanumeric design.

10. The device of claim 6, wherein said nail reinforcing device sides are shaped to substantially match the curvature of the top surface of the natural fingernail.

11. A method of reattaching a broken fingernail comprising:
    providing a pliable nail reinforcing device having a body, a first side, a second side, and an upper surface;
    applying an adhesive to at least a portion of an underneath surface of a detached portion and a remaining portion of broken fingernail or said upper surface of said pliable nail reinforcing device;
    conforming said body of said pliable nail reinforcing device to the curvature of the underneath surface of the natural fingernail so as to provide contact between said upper surface of said pliable nail reinforcing device and an underneath surface of said detached portion of the broken fingernail;
    positioning said pliable nail reinforcing device so as to provide contact between said upper surface of said pliable nail reinforcing device and an underneath surface of the remaining portion of the broken fingernail;

folding said first side and said second side of said pliable nail reinforcing device so as to provide substantially conforming contact between a top surface of the natural fingernail and said upper surface of said pliable nail reinforcing device; and maintaining said nail reinforcing device in a stable position to ensure adherence between said upper surface of said nail reinforcing device and the underneath surfaces of the detached portion and remaining portion of the broken fingernail.

12. The method of claim 11, further comprising shaping said body of said pliable nail reinforcing device to conform to the contour of the underneath surface of the detached portion and the remaining portion of the broken fingernail prior to applying an adhesive to the underneath surfaces of the detached portion and the remaining portion of the broken fingernail.

13. The method of claim 11, further comprising shaping said first and second sides of said pliable nail reinforcing device to conform to the contour of the top surface of the detached portion and remaining portion of the broken fingernail after conforming said body of said pliable nail reinforcing device to the curvature of the underneath surface of the natural fingernail.

14. The method of claim 11, wherein said nail reinforcing device has a thickness that is less than the thickness of the natural fingernail.

15. The method of claim 11, wherein said first and second sides of said pliable nail reinforcing device are shaped to form a decorative pattern on said top surface of the natural fingernail.

16. A method of repairing a damaged fingernail comprising:

providing a pliable nail reinforcing device having a body, a first side, a second side, and an upper surface;

applying an adhesive to at least a portion of an underneath surface of the damaged fingernail or said upper surface of said pliable nail reinforcing device;

conforming said body of said pliable nail reinforcing device to the curvature of the underneath surface of the natural fingernail so as to provide contact between said upper surface of said pliable nail reinforcing device and the underneath surface of the damaged fingernail;

maintaining said nail reinforcing device in a stable position to ensure adherence between said upper surface of said nail reinforcing device and the underneath surface of the natural fingernail;

applying a material to a portion of said nail reinforcing device underlying a damaged portion of the damaged fingernail to fill the damaged portion of the damaged fingernail;

folding said first side and said second side of said pliable nail reinforcing device so as to provide substantially conforming contact between a top surface of the damaged fingernail and said upper surface of said pliable nail reinforcing device; and maintaining said nail reinforcing device in a stable position to ensure adherence between said upper surface of said pliable nail reinforcing device and the top surface of the damaged fingernail.

17. The method of claim 16, further comprising shaping said body of said pliable nail reinforcing device to conform to the contour of the underneath surface of a damaged fingernail prior to applying an adhesive to the underneath surface of the damaged fingernail.

18. The method of claim 16, further comprising shaping said first and second sides of said pliable nail reinforcing device to conform to the contour of the top surface of the damaged natural fingernail after conforming said body of said pliable nail reinforcing device to the curvature of the underneath surface of the damaged fingernail.

19. The method of claim 16, wherein said adhesive is applied to at least a portion of an underneath surface of the damaged fingernail, to at least a portion of a top surface of the damaged fingernail, and to at least a portion of said upper surface of said pliable nail reinforcing device.

20. The method of claim 16, wherein said first and second sides of said pliable nail reinforcing device are shaped to form a decorative pattern on said top surface of the natural fingernail.

* * * * *